United States Patent [19]

Plunkett et al.

[11] 4,163,025

[45] Jul. 31, 1979

[54] PROCESS FOR THE PRODUCTION OF BENZYLAMINE AND DIBENZYLAMINE

[75] Inventors: Richard A. Plunkett, Elkhart; Jerry L. Neff, Nappanee; Timothy A. Bemish, Bremen, all of Ind.

[73] Assignee: Miles Laboratories, Inc., Elkhart, Ind.

[21] Appl. No.: 541,494

[22] Filed: Jan. 16, 1975

[51] Int. Cl.² .............................................. C07C 85/12
[52] U.S. Cl. ............................ 260/570.9; 260/570.8 R
[58] Field of Search .................... 260/570.9, 570.8, 580

[56] References Cited

U.S. PATENT DOCUMENTS

| 3,069,469 | 12/1962 | Wilkes | 260/570.9 |
| 3,117,162 | 1/1964 | Rylander et al. | 260/570.9 X |
| 3,194,839 | 7/1965 | Robinson et al. | 260/580 X |
| 3,467,710 | 9/1969 | Kaltenbronn | 260/570.8 |
| 3,578,720 | 5/1971 | Dodman et al. | 260/580 UX |

OTHER PUBLICATIONS

Wagner et al., "Synthetic Organic Chemistry," pp. 658–660 (1953).

Primary Examiner—Winston A. Douglas
Assistant Examiner—John Doll
Attorney, Agent, or Firm—Richard W. Winchell

[57] ABSTRACT

A process is provided for preparing benzylamine and dibenzylamine by passing benzonitrile and hydrogen counter-currently through a catalyst bed under suitable conditions of temperature and pressure to hydrogenate the benzonitrile and thereby produce the desired reaction product.

7 Claims, No Drawings

PROCESS FOR THE PRODUCTION OF BENZYLAMINE AND DIBENZYLAMINE

BACKGROUND AND PRIOR ART

The arylalkyl amines, in particular benzylamine and dibenzylamine are important industrial organic compounds. Benzylamine is a primary amine which is useful as a corrosion inhibitor. Dibenzylamine is a secondary amine which finds use in the production of synthetic penicillins and in the vulcanization of rubber.

Numerous procedures for the production of these amines are described in the literature and include: the reductive amination of benzaldehyde by hydrogen and ammonia in the presence of a catalyst; the catalytic reduction of benzonitrile or benzylhydroxylamine; or the condensation of benzaldehyde and benzylamine followed by catalytic hydrogenation of the intermediate Schiff's base. Generally, benzylamine and dibenzylamine are obtained in poor yield and each amine must be carefully separated from mixtures containing primary, secondary or tertiary amines, imines, aldehydes, alcohols or amides to obtain a high purity product.

For example, it is known that nitriles can be catalytically reduced to the primary amine through the intermediate imine by a wide variety of catalysts as follows:

The intermediate imine further reacts with the primary amine to produce a Schiff's base with the liberation of ammonia,

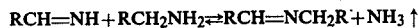

In the presence of a catalyst and hydrogen, the Schiff's base is further reduced to the secondary amine,

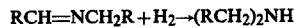

In a batch process, the above reactions compete for reactants and a variety of reaction products are formed. Many means have been employed to minimize the extent of these reactions including reduction in very dilute organic solvent solutions, solvent selection and catalyst selection. Rylander et al. disclose, in U.S. Pat. No. 3,117,162 and Annals N.Y. Acad. Sci. 214:100-109(1973), a batch process for the reduction of benzonitrile in dilute organic solvent solutions such as hexane, octane, ethanol and benzene by hydrogenation over rhodium, palladium, platinum, or ruthenium catalysts (all 5% on carbon). At best, Rylander et al. obtain benzylamine at 63% yield from a mixed reaction product containing 34% of the secondary amine. The production of dibenzylamine is favored in this process by the selective use of rhodium on carbon or platinum on carbon catalysts, but in all other cases it is obtained as a mixture containing large amounts of the primary amine. In addition, long reaction times, 2 to 21 hours, are required to reduce the benzonitrile and the reaction products must be further separated from very dilute organic solvent solutions. Similarly, Takagi et al. in Sci. Papers Inst. Phys. Chem. Res. 61(3), 114-117(1967), disclose a batch process for the reduction of benzonitrile in ethanol over 3:1 iridium platinum oxide catalyst. This reaction produces about 42% benzylamine and 50% dibenzylamine. In each case long reaction times are required and the reaction products must be separated from very dilute solutions. As a result, these prior art techniques are time consuming and costly.

SUMMARY OF THE INVENTION

In accordance with the present invention, a novel process is provided for the preparation of a reaction product selected from the class consisting of benzylamine and dibenzylamine, which comprises passing benzonitrile and hydrogen countercurrently through a catalyst bed under suitable conditions of temperature and pressure to thereby hydrogenate the benzonitrile and produce the desired reaction product.

DESCRIPTION OF THE INVENTION

In the practice of this invention in the preferred manner, the catalyst is charged into any suitable vertical trickle bed reactor column capable of being heated under moderate pressures, to form a catalyst bed. Examples of such useful catalysts include Raney nickel pellets, zirconium promoted reduced nickel on Kieselguhr tablets, platinum on alumina tablets and the like. It is preferred to use Raney nickel pellets. It will be understood by those skilled in the art that reactor columns will vary in overall length and diameter and the catalyst bed depth may be varied accordingly without affecting the yield or purity of the desired reaction product obtained.

Benzonitrile is fed into the top of the reactor column through a suitable feeding device. At the same time hydrogen is introduced at the bottom of the reactor column at a pressure sufficient to produce the desired reaction product. The benzonitrile and the hydrogen thus flow countercurrently within the reactor bed, the downwardly flowing liquid being thoroughly contacted by the upwardly flowing hydrogen within the catalyst bed. The reactor column and contents are heated by any suitable means up to a temperature sufficient to promote hydrogenation of the benzonitrile in the presence of the catalyst and hydrogen. Usually a temperature between about 50° and 175° C. is sufficient. Higher temperatures tend to produce an undesirable colored product of lower than desired purity. The ratio of the input stream of hydrogen flow (measured at S.T.P.) to the input stream of benzonitrile flow based upon the volumes passed per unit of time can be varied depending upon the desired reaction product to be produced. When benzonitrile and hydrogen are continuously fed into the reactor column, the desired reaction product is produced in the reactor column and is continuously removed from the bottom thereof. Suitable controls and mechanical devices as will be understood by those skilled in the art are provided to permit control of flow rates, temperatures and pressures and thereby maintenance of steady state operation.

The production of the desired reaction product, as stated above, is dependent upon the pressures and the ratios of hydrogen stream flow to benzonitrile stream flow selected. When benzylamine is the desired reaction product to be produced, pressures of greater than about 115 p.s.i.a. and flow ratios of hydrogen to benzonitrile of less than about 600 based upon the relative volumes passed per unit of time are usually found to be sufficient. Flow ratios of hydrogen to benzonitrile of about 420 to 460 based upon the relative volumes passed per unit of time are preferred. Under these conditions, ammonia which is liberated during the course of the reaction accumulates in the column and as a result at equilibrium the reaction is shifted toward the production of primary amine and benzylamine is the principal reaction product. When dibenzylamine is the desired reaction product to be produced, pressures of less than about 115 p.s.i.a. and flow ratios of hydrogen to benzonitrile of greater than about 600 based upon the relative volumes passed per unit of time are usually found to be sufficient. The upper limit of flow ratios of hydrogen to benzonitrile is only limited by the cost of raw materials and recovery of excess hydrogen. Under these conditions, ammonia which is liberated during the course of the reaction is swept from the reactor column by the excess hydrogen flowing therethrough and as a result at equilibrium the reaction is shifted toward the production of secondary amine and dibenzylamine is the principal reaction product.

The following examples are given to further illustrate the method of preparing benzylamine and dibenzylamine and are not intended to limit the invention.

EXAMPLE 1

This example demonstrates the operation of a continuous countercurrent reactor system employing a small scale trickle bed reactor column, approximately 42 inches in length by 1 inch in diameter.

Raney nickel pellets, Grade 5842- crushed, granular nickel-aluminum alloy having the dimensions of about ¼ in. × ⅛ in., supplied by the Davison Chemical Division of W. R. Grace Co., were activated in the conventional manner by leaching about 10 to 12% of the original aluminum content from the surface of the pellets with an aqueous solution of about 7 to 25% by weight, of sodium hydroxide. The pellets were washed with water, followed by further washing with methanol and benzonitrile. About 925 grams of the thus-activated Raney nickel pellets were then charged into the reactor column to a bed depth of about 37 inches.

A. Preparation of Benzylamine

Unidiluted, high purity benzonitrile was introduced at the top of the reactor column, prepared in manner described above, at a constant feed rate of 24 ml. per hour, and hydrogen was introduced at the bottom of the reactor column at a constant flow rate of 10.6 liters (S.T.P.) per hour at a pressure of 165 p.s.i.a. This corresponds to a countercurrent flow ratio of hydrogen-to-benzonitrile of about 440 based upon the volumes passed per unit of time. The column and contents were heated to 100° C. After a steady state condition was achieved, samples of the effluent stream were taken from the bottom of the reactor and analyzed by gas chromatography. The percentages of reaction products as determined by gas chromatography in the following examples express the percent by weight. The effluent stream was composed of 93.2% benzylamine, 5.2% dibenzylamine, and about 1.6% unknown.

The above procedure was repeated at a pressure of 215 p.s.i.a. After a steady state condition was achieved, samples of the effluent stream were taken from the bottom of the reactor and analyzed by gas chromatography. The effluent stream was composed of 94.6% benzylamine and 5.4% dibenzylamine.

B. Preparation of Dibenzylamine

Unidiluted, high purity benzonitrile was introduced at the top of the reactor column, prepared in the same manner as described above, at a constant feed rate of 30 ml. per hour, and hydrogen was introduced at the bottom of the reactor column at a constant flow rate of 73.7 liters (S.T.P.) per hour at a pressure of 75 p.s.i.a. This corresponds to a countercurrent flow ratio of hydrogen-to-benzonitrile of about 2450, based upon the volumes passed per unit of time. The column and contents were heated to 100° C. After a steady state condition was achieved, samples of the effluent stream were taken from the bottom of the reactor and analyzed by gas chromatography. The effluent stream was composed of 95.3% dibenzylamine, 1.0% benzylamine, 1.0% tribenzylamine, 1.9% cyclohexanemethylbenzylamine, and 0.8% Schiff's base.

The above procedure was repeated at a constant benzonitrile flow rate of 15 ml. per hour and a constant hydrogen flow rate of 121 liters (S.T.P.) per hour at a pressure of 60 p.s.i.a. This corresponds to a countercurrent flow ratio of hydrogen-to-benzonitrile of about 8070 based upon the volumes passed per unit of time. The column and contents were heated to 100° C. After a steady state condition was achieved, samples of the effluent stream were taken and analyzed by gas chromatography. The effluent stream was composed of 94.6% dibenzylamine, 0.9% benzylamine, 1.1% tribenzylamine, 2.8% cyclohexanemethylbenzylamine and 0.4% Schiff's base.

EXAMPLE 2

This example demonstrates the operation of a continuous countercurrent reactor system employing a pilot scale trickle bed reactor column, approximately 72 inches in length by 4 inches in diameter.

About 26 kg. of Raney nickel pellets activated in the conventional manner described in Example 1 were charged into the reactor column to a bed depth of about 66 inches. Undiluted, high purity benzonitrile was then introduced at the top of the reactor column at a constant feed rate of 1080 ml. per hour, and hydrogen was introduced at the bottom of the reactor at a constant flow rate of 1152 liters (S.T.P.) per hour at a pressure of 55 p.s.i.a. This corresponds to a countercurrent flow ratio of hydrogen-to-benzonitrile of about 1067, based upon the volumes passed per unit of time. The column and contents were heated to 100° C. After a steady state condition was achieved, samples of the effluent stream were taken from the bottom of the reactor and analyzed by gas chromatography. The effluent stream was composed of 92.8% dibenzylamine, 1.8% benzylamine, 2.0% tribenzylamine and 1.7% cyclohexanemethylbenzylamine. No benzonitrile and only 1.5% of Schiff's base were found.

EXAMPLE 3

A small scale trickle bed reactor column, approximately 42 inches in length by 1 inch in diameter, was prepared in the following manner. About 1000 grams of Girdler G-69, zirconium promoted reduced nickel on kieselguhr tablets, having the dimensions of about 3/16 in. × ⅛ in., supplied by Chemetron Chemicals Division of Chemetron Corporation, were charged into the reactor column to a bed depth of about 40 inches.

Undiluted, high purity benzonitrile was introduced at the top of the reactor column at a constant feed rate of 18 ml. per hour and hydrogen was introduced at a constant flow rate of about 8.0 liters (S.T.P.) per hour at a pressure of 265 p.s.i.a. This corresponds to a countercurrent flow ratio of hydrogen to benzonitrile of about 440, based upon the volumes passed per unit of time. The column and contents were heated to about 100° C. After a steady state condition was achieved, samples of the effluent stream were taken and analyzed by gas chromatography. The effluent stream was composed of 92.7% benzylamine, 5.5% dibenzylamine, 0.1% tribenzylamine, 0.8% benzonitrile, and 0.8% unknown.

EXAMPLE 4

About 875 grams of 1% platinum on alumina tablets, 3/16 in.×⅛ in., supplied by Englehard Industries Division, were charged into a small trickle bed reactor column to a bed depth of about 35 inches. Undiluted high purity benzonitrile was then introduced at the top of the reactor column at a constant feed rate of 42 ml. per hour, and hydrogen was introduced at the bottom of the reactor column at a constant flow rate of 108 liters (S.T.P.) per hour at a pressure of 95 p.s.i.a. This corresponds to a countercurrent flow ratio of hydrogen to benzonitrile of about 2570, based upon the volumes passed per unit of time. The column and contents were heated to 100° C. After a steady state condition was achieved, samples of the effluent stream were taken from the bottom of the reactor and analyzed by gas chromatography. The effluent stream was composed of 89.2% dibenzylamine, 0.1% benzylamine, 0.8% benzonitrile and 8.6% of a mixture of cyclohexanemethylbenzylamine and dicyclohexanemethylamine.

What is claimed is:

1. A process for preparing benzylamine, which comprises passing undiluted benzonitrile and hydrogen countercurrently through a catalyst bed, wherein the catalyst is selected from the class consisting of Raney nickel, zirconium promoted reduced nickel and platinum, under suitable conditions of temperature and pressure to thereby hydrogenate the benzonitrile and produce the desired reaction product, wherein the pressure is greater than about 115 p.s.i.a. and the ratio of hydrogen flow to benzonitrile flow based upon the relative volumes passed per unit of time in countercurrent fashion is less than about 600.

2. A process according to claim 1, wherein the ratio of hydrogen flow to benzonitrile flow is between about 420 and 460.

3. A process according to claim 1, wherein the catalyst consists essentially of Raney nickel.

4. A process according to claim 1, wherein the catalyst consists essentially of zirconium promoted-reduced nickel.

5. A process for preparing dibenzylamine, which comprises passing undiluted benzonitrile and hydrogen countercurrently through a catalyst bed, wherein the catalyst is selected from the class consisting of Raney nickel, zirconium promoted reduced nickel and platinum, under suitable conditions of temperature and pressure to thereby hydrogenate the benzonitrile and produce the desired reaction product, wherein the pressure is less than about 115 p.s.i.a. and the ratio of hydrogen flow to benzonitrile flow based upon the relative volumes passed per unit of time in countercurrent fashion is greater than about 600.

6. A process according to claim 5, wherein the catalyst consists essentially of Raney nickel.

7. A process according to claim 5, wherein the catalyst consists essentially of platinum.

* * * * *